United States Patent
Haesloop

(10) Patent No.: US 8,057,333 B2
(45) Date of Patent: Nov. 15, 2011

(54) SERIES SPRING BLADE TENSIONER

(75) Inventor: J. Christian Haesloop, Ithaca, NY (US)

(73) Assignee: BorgWarner Inc., Auburn Hills, MI (US)

( * ) Notice: Subject to any disclaimer, the term of this patent is extended or adjusted under 35 U.S.C. 154(b) by 539 days.

(21) Appl. No.: 12/296,126

(22) PCT Filed: Mar. 30, 2007

(86) PCT No.: PCT/US2007/065567
§ 371 (c)(1),
(2), (4) Date: Oct. 6, 2008

(87) PCT Pub. No.: WO2007/121068
PCT Pub. Date: Oct. 25, 2007

(65) Prior Publication Data
US 2009/0163311 A1    Jun. 25, 2009

Related U.S. Application Data

(60) Provisional application No. 60/744,617, filed on Apr. 11, 2006.

(51) Int. Cl.
*F16H 7/08* (2006.01)
*F16H 7/18* (2006.01)
(52) U.S. Cl. ...................................................... 474/111
(58) Field of Classification Search ................... 474/101, 474/109, 110, 11, 140, 111
See application file for complete search history.

(56) References Cited

U.S. PATENT DOCUMENTS

| | | | |
|---|---|---|---|
| 3,426,606 A | 2/1969 | Hopkins | |
| 4,921,472 A | 5/1990 | Young | |
| 5,055,088 A | 10/1991 | Cradduck et al. | |
| 5,797,818 A | 8/1998 | Young | |
| 5,984,815 A | 11/1999 | Baddaria | |
| 6,361,459 B1 | 3/2002 | Serkh et al. | |
| 6,524,202 B1 * | 2/2003 | Tada et al. | 474/109 |
| 6,623,391 B2 | 9/2003 | Young et al. | |
| 7,163,478 B2 | 1/2007 | Oliver et al. | |
| 7,163,479 B2 | 1/2007 | Young | |
| 2002/0045503 A1 | 4/2002 | Young et al. | |
| 2002/0069539 A1 | 6/2002 | Tada | |
| 2002/0142872 A1 | 10/2002 | Tada | |
| 2003/0125144 A1 | 7/2003 | Horikawa et al. | |
| 2004/0005953 A1 | 1/2004 | Yonezawa et al. | |
| 2005/0143207 A1 * | 6/2005 | Hashimoto et al. | 474/109 |

FOREIGN PATENT DOCUMENTS

| | | |
|---|---|---|
| DE | 1500447 | 6/1970 |
| EP | 1030078 | 8/2000 |

(Continued)

OTHER PUBLICATIONS

PCT Search Report; PCT/US2007/065567; Aug. 6, 2007, 12 pages.

*Primary Examiner* — William W Dondero
(74) *Attorney, Agent, or Firm* — Brown & Michaels, PC

(57) ABSTRACT

A blade tensioner includes a blade shoe assembly with parallel stacked flat springs that pivots at one end and is supported in series by a spring loaded ramp at the opposite end. Providing a spring loaded ramp in series reduces the overall stiffness of the tensioner which enables a more uniform tensioning load as the tensioner takes up chain slack due to elongation from wear.

19 Claims, 3 Drawing Sheets

FOREIGN PATENT DOCUMENTS

| | | |
|---|---|---|
| EP | 1323949 | 7/2003 |
| EP | 1338827 | 8/2003 |
| EP | 1452774 | 9/2004 |
| GB | 1077715 | 8/1967 |
| GB | 1085213 | 9/1967 |
| GB | 1290279 | 9/1972 |
| JP | 2003065404 | 3/2003 |
| JP | 2003322226 | 11/2003 |
| JP | 2004028346 | 1/2004 |
| JP | 2005325855 | 11/2005 |

\* cited by examiner

US 8,057,333 B2

SERIES SPRING BLADE TENSIONER

REFERENCE TO RELATED APPLICATIONS

This application claims an invention which was disclosed in Provisional Application No. 60/744,617, filed Apr. 11, 2006, entitled "SERIES SPRING BLADE TENSIONER". The benefit under 35 USC §119(e) of the U.S. provisional application is hereby claimed, and the aforementioned application is hereby incorporated herein by reference.

BACKGROUND OF THE INVENTION

1. Field of the Invention

The invention pertains to the field of spring blade tensioners. More particularly, the invention pertains to a series spring blade tensioner.

2. Description of Related Art

A conventional blade spring tensioner may develop adequate force to control the new chain condition but lack sufficient force to control the worn chain condition. In order to develop sufficient tensioning load in a compact package, conventional tensioners may have a high system spring rate. A system with a high spring rate is highly sensitive to deflection. Consequently, the applied tensioning load may decrease too rapidly with a high system spring rate as the blade assembly deflects to take up chain slack. One solution is to increase the tensioning load for a new chain such that a minimum acceptable load is achieved when the chain is in the worn chain condition. This approach is undesirable since high tensioning loads for a new chain cause greater frictional losses, increased chain engagement noise and higher blade shoe and chain wear.

SUMMARY OF THE INVENTION

In order to develop sufficient tensioning load in a compact package, conventional blade tensioners may have a high system spring rate. The applied tensioning load may decrease too rapidly with a high system spring rate as the blade assembly deflects to take up chain slack. The blade tensioner of the present invention includes a blade shoe assembly with parallel stacked blade springs that pivots at one end and is supported in series by a spring loaded ramp at the opposite end. Providing a spring loaded ramp in series reduces the overall stiffness of the tensioner which enables a more uniform tensioning load as the tensioner takes up chain slack due to elongation from wear.

DETAILED DESCRIPTION OF THE INVENTION

Figure 1:
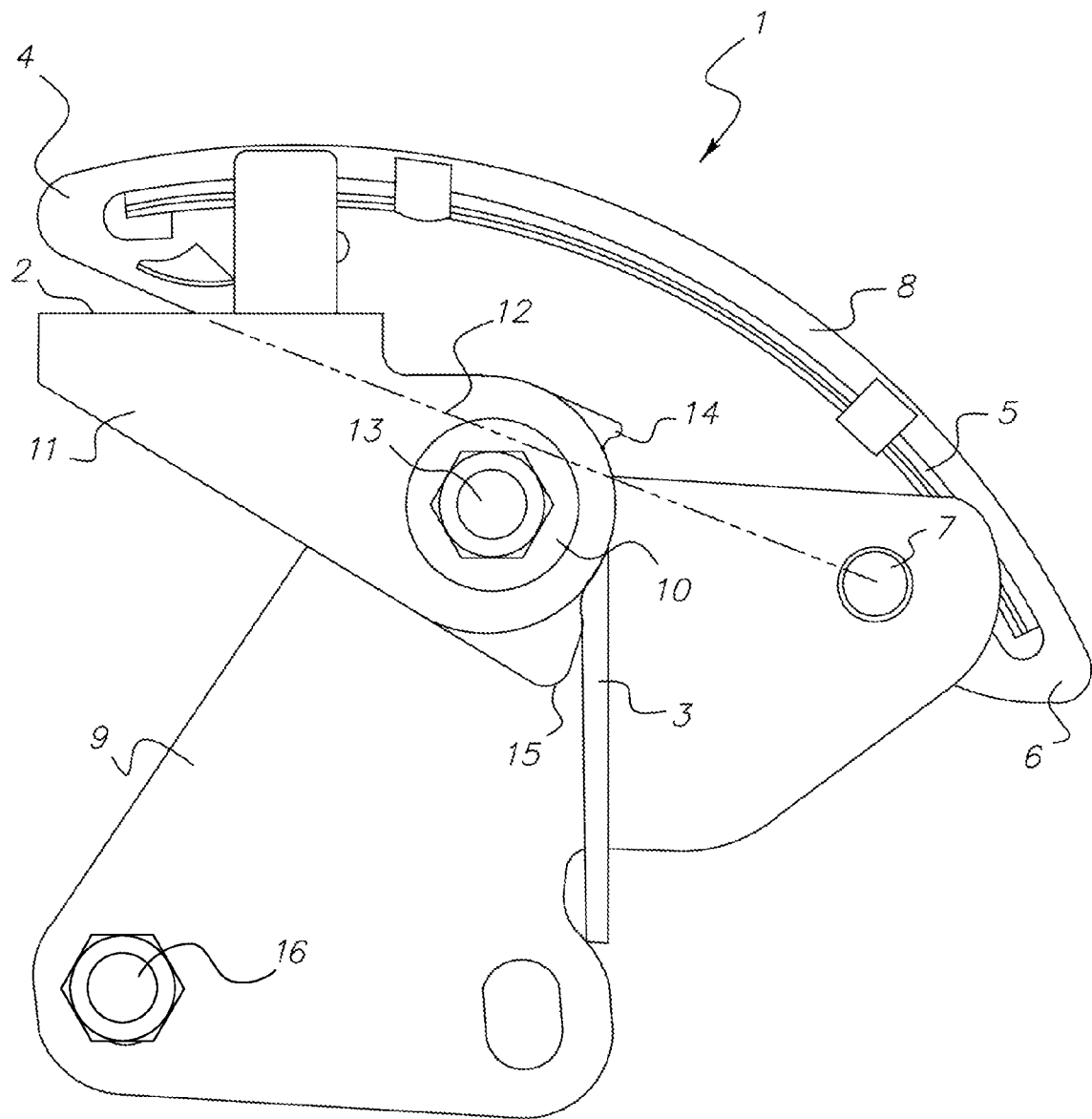
FIG. 1 shows a side view of a tensioner in an embodiment of the present invention.

The present invention relates to the problem of maintaining adequate tensioning load on a chain as the chain elongates due to wear. The present invention includes a blade shoe assembly with parallel stacked springs that pivots at one end and is supported in series by a spring loaded ramp at the opposite end. In one preferred embodiment, the ramp assembly spring is a torsion spring. Providing a spring loaded ramp in series reduces the overall stiffness of the tensioner. The force developed by the torsion spring balances the force generated by the free end of the blade shoe assembly.

A conventional blade tensioner has a blade shoe with multiple flat springs that are assembled in parallel. The effective total spring constant of multiple springs assembled in parallel is equal to the sum of each individual spring. For example, four springs of equal spring rate constant combined in parallel give an effective total spring rate of $k(parallel)=k(1)+k(2)+k(3)+k(4)$. The present invention incorporates an additional spring that is arranged in series with the blade shoe assembly. The inverse of the effective total spring rate constant of two springs assembled in series is equal to the sum of the inverses of each individual spring or $1/k(series)=1/k(1)+1/k(2)$. Therefore, arranging springs in parallel increases total stiffness while arranging springs in series decreases stiffness. The present invention reduces the spring rate of the tensioner system, which makes the tensioner less sensitive to deflection. This creates a more uniform tensioning load as the tensioner takes up chain slack due to elongation.

A series spring tensioner for controlling chains used in automotive engines includes one or more parallel stacked blade springs assembled into a wear-resistant shoe. In one embodiment, the blade shoe is mounted to a bracket with a pivot mechanism. In another embodiment, the blade shoe and the ramp assembly are mounted directly to the engine. The pivot mechanism is preferably a pivot pin. In alternative embodiments, the pivot mechanism may be cylindrical pockets, ball joints, or any pivot mechanism that would permit the blade shoe to pivot effectively.

In a preferred embodiment, the shoe is made of plastic. In another embodiment, the bracket is preferably a stationary stamped steel bracket. The pivot pin is preferably made of steel. The shoe has a pivot end and a free sliding end which reacts against a spring loaded ramp assembly. The shoe is assembled to the bracket and is retained by the pivot pin. The ramp assembly preferably includes a steel stamping provided with a flat planar surface for the shoe to react against, pivot holes integral with the ramp stamping, a pivot bushing for the ramp to oscillate about and a ramp assembly spring to provide torque to the ramp. The spring is preferably a torsion spring, but may alternatively be any other type of spring capable of providing torque to the system. The pivot bushing is preferably made of steel. In one embodiment, the pivot bushing is clamped by a fastener, such as a bolt, that is also common for mounting the tensioner bracket to the engine. In another embodiment, a separate pivot pin is used for ramp rotation independent of the mounting bolt used for bracket mounting.

The ramp stamping is also designed to limit the rotational travel of the ramp in each direction within specified limits. Back travel due to high chain load is preferably controlled with a physical stop to limit excessive chain motion. Forward travel into the chain is preferably controlled with another physical stop to prevent the ramp assembly spring from total load relaxation and fix the ramp in a stable position for assembly to the engine.

One embodiment of the present invention incorporates a steel bracket and a steel ramp with a steel pivot pin for the blade and a steel pivot bushing for the torsion spring ramp. The bracket and ramp may also be made from alternate materials with sufficient structural and wear integrity including, but not limited to, die cast aluminum or glass filled nylon molded with metal mounting bolt and pivot inserts. In another embodiment, the bracket is eliminated altogether with the blade pivot pin and the torsion spring ramp pivot details located directly on the engine. In other embodiments, the pivot pin may be replaced with alternate pivot joint geometries including, but not limited to, cylindrical pockets or ball joints.

Figure 2:
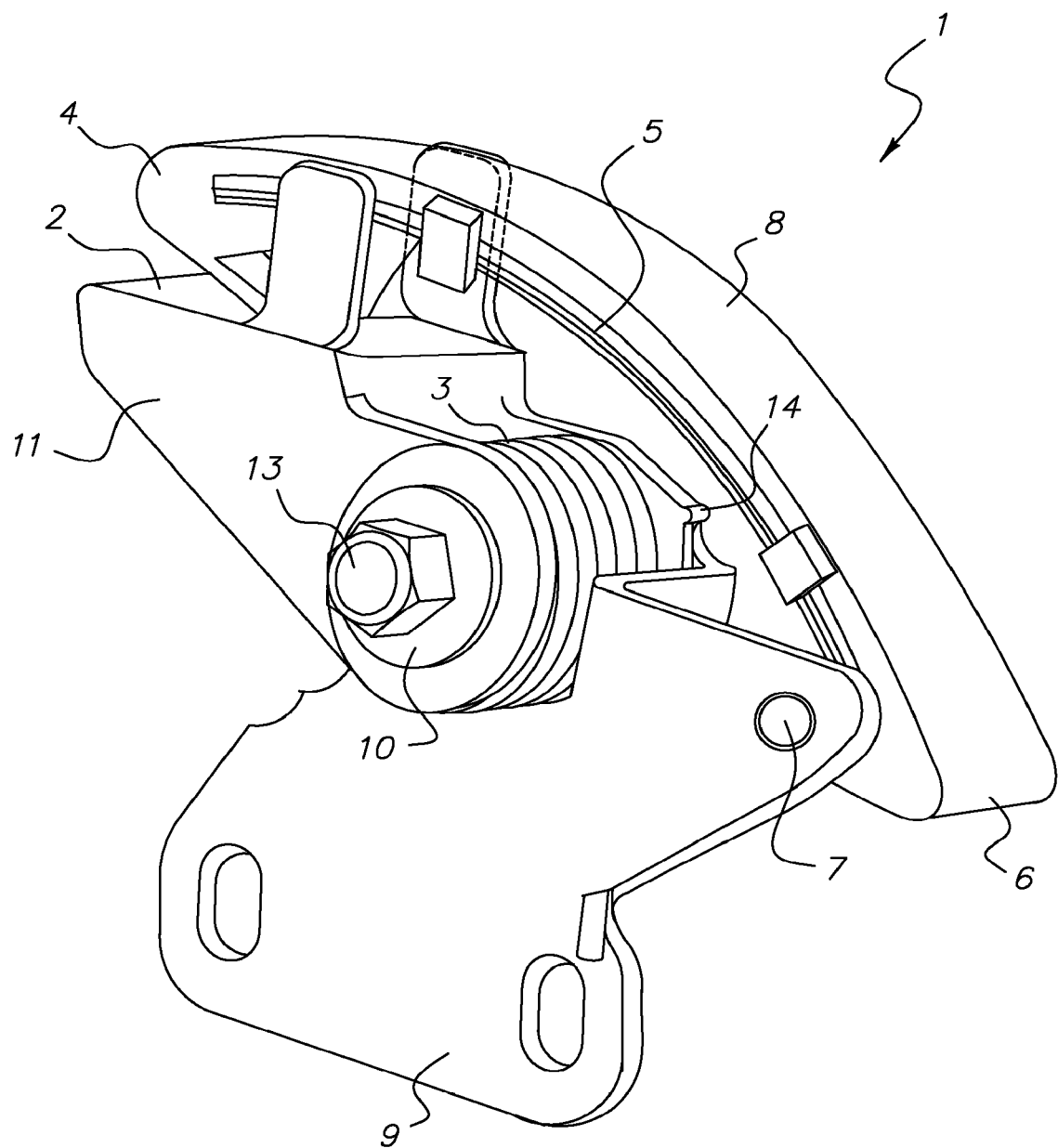
FIG. 2 shows another view of a tensioner in an embodiment of the present invention.
Figure 3:
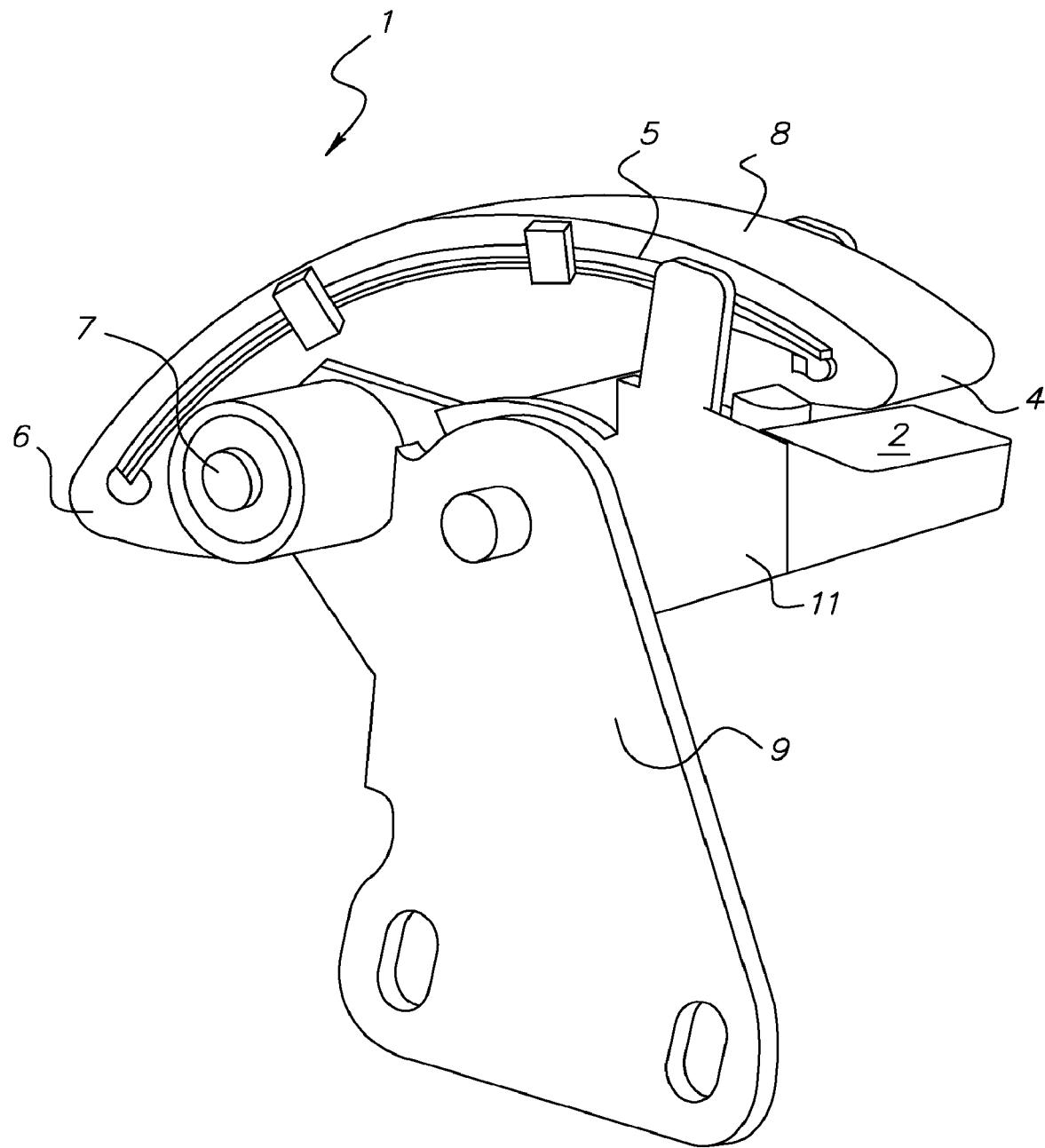
FIG. 3 shows another view of the tensioner in an embodiment of the present invention.

Referring to FIGS. 1 through 3, a tensioner (1) includes a blade shoe (8) with one or more parallel stacked blade springs (5). The blade springs (5) are preferably flat. Although four blade springs (5) are shown in the figures, any number of springs could be used. The shoe (8) is mounted on a bracket (9) with a pivot pin (7). In FIG. 1, a mounting bolt (16) mounts the bracket (9) to an engine. The shoe (8) has a pivot end (6) and a free sliding end (4). In a preferred embodiment, the shoe (8) is made of plastic. In another preferred embodiment, the bracket (9) is made of stamped steel. In yet another preferred embodiment, the pivot pin is made of steel.

The blade shoe (8) has a pivot end (6) and a free sliding end (4). A spring loaded ramp assembly (11) has a planar surface (2) against which the blade shoe (8) slides. The free sliding end (4) of the blade shoe (8) reacts against the torsion spring loaded ramp assembly (11). Although a torsion spring is shown in the figures, any type of spring including, but not limited to, a helical compression spring, an extension spring, or a leaf spring, could be used. The ramp assembly (11) pivots about a bushing (10), which is preferably cylindrical. The pivot bushing (10) is preferably clamped by a fastener (13), such as a bolt.

In one embodiment, back travel due to high chain load is preferably controlled with a physical stop (15) to limit excessive chain motion. Forward travel into the chain is preferably controlled with another physical stop (14) to prevent the torsion spring (3) from total load relaxation and fix the ramp in a stable position for assembly to the engine. Although both a back travel stop (15) and a forward travel stop (14) are shown in the figures, alternative embodiments of the series spring blade tensioner may omit the back travel stop (15) and/or the forward travel stop (14).

As the ramp assembly (11) rotates to maintain total spring load balance, the ramp planar surface (2) orientation changes. Ramp surface (2) orientation with respect to the sliding end (4) of the blade shoe (8) is another factor which determines overall effective stiffness of the tensioner (1). High effective stiffness occurs when the ramp surface (2) is parallel to a chordal line (12) drawn from the pivoting end to the free end of the blade shoe. More specifically, the chordal line (12) is drawn from the pivot point on the pivot end (6) of the blade shoe (8) to the point where the nose of the sliding end (4) of the blade shoe (8) contacts the ramp (2). Lower effective stiffness occurs as the ramp surface (2) rotates away from the defined parallel position. The ramp surface (2) is closest to the parallel position when the ramp assembly has moved forward and has reached the forward travel stop (14). The ramp surface (2) is farthest from the parallel position when the ramp assembly has moved backward and has reached the back travel stop (15).

The bracket (9) is mounted to the engine such that the blade spring(s) (5) and shoe blade assembly push against the slack strand of the chain (not shown). The spring force constants of the blade springs and the ramp assembly spring are selected to respond to varying chain load conditions. The blade shoe assembly deflects, oscillates about the pivot end (6), slides on the ramp planar surface (2), and follows the motion of the ramp surface (2) as the ramp (11) rotates.

High chain loads flatten the arc of the blade shoe assembly, cause the blade free end (4) to slide down the ramp (11) and cause the ramp (11) to rotate, increasing the resisting torque of the ramp torsion spring (3) until the spring system achieves force balance. Low chain loads reverse the actions, the blade shoe arc radius decreases, the blade free end (4) slides up the ramp (2) and the ramp assembly (11) rotates, decreasing resisting torque of the torsion spring (3) until the system again achieves force balance.

The present invention recognizes that there are many design variables that can be tuned to achieve optimum performance of the overall tensioner system. Tuning variables are the force and stiffness of the blade shoe assembly as well as the ramp assembly, location of the blade shoe pivot and the ramp pivot, ramp surface location and orientation, and blade assembly arc and arc length. Each of these variables can be tuned to achieve the optimum balance of overall tensioner force and stiffness.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A tensioner for a chain used in an automotive engine, comprising:
    a) a bracket;
    b) a blade shoe having a first end and a second end, wherein the first end of the blade shoe is mounted on the bracket with a first pivot mechanism;
    c) at least one blade spring assembled into the blade shoe; and
    d) a spring loaded ramp assembly comprising:
        a ramp having a planar surface upon which the second end of the blade shoe slides;
        a second pivot mechanism by which the ramp is rotatable; and
        a ramp assembly spring to provide torque to the ramp to balance a force on the ramp generated by the second end of the blade shoe;
    wherein the blade spring and the spring loaded ramp assembly support the blade shoe in series.

2. The tensioner of claim 1, wherein the spring loaded ramp assembly is connected to the bracket.

3. The tensioner of claim 1, wherein the second pivot mechanism comprises a pivot bushing.

4. The tensioner of claim 3, wherein the pivot bushing is made of steel.

5. The tensioner of claim 1, further comprising a fastening mechanism that fastens the second pivot mechanism and mounts the tensioner to the engine.

6. The tensioner of claim 1, wherein the first pivot mechanism is a pivot pin made of steel.

7. The tensioner of claim 1, further comprising at least one mounting bolt that mounts the bracket to the engine.

8. The tensioner of claim 1, wherein the blade shoe is made of plastic.

9. The tensioner of claim 1, wherein the bracket is a stationary stamped steel bracket.

10. The tensioner of claim 1, wherein the ramp is made of steel.

11. The tensioner of claim 1, wherein the blade spring comprises a plurality of blade springs assembled in parallel.

12. The tensioner of claim 1, wherein the ramp assembly spring is a torsion spring.

13. The tensioner of claim 1, wherein the spring force constants of the blade spring and the ramp assembly spring are selected such that, when the tensioner is exposed to high chain loads, the blade shoe flattens and the second end of the blade shoe slides down the ramp such that the ramp rotates and increases a resisting torque of the ramp assembly spring until the ramp assembly spring and the blade spring achieve a force balance.

14. The tensioner of claim 1, wherein the spring force constants of the blade spring and the ramp assembly spring are selected such that, when the tensioner is exposed to low chain loads, an arc radius of the blade shoe decreases and the second end of the blade shoe slides up the ramp such that the ramp rotates and decreases a resisting torque of the ramp assembly spring until the ramp assembly spring and the blade spring achieve a force balance.

15. A tensioner for a chain used in an automotive engine, comprising:
 a) a blade shoe having a first end and a second end, wherein the first end of the blade shoe is mounted on the engine with a first pivot mechanism;
 b) at least one blade spring assembled into the blade shoe; and
 c) a spring loaded ramp assembly comprising:
  a ramp having a planar surface upon which the second end of the blade shoe slides;
  a second pivot mechanism by which the ramp is rotatable; and
  a ramp assembly spring to provide torque to the ramp to balance a force on the ramp generated by the second end of the blade shoe;
  wherein the blade spring and the spring loaded ramp assembly support the blade shoe in series.

16. The tensioner of claim 15, wherein the spring loaded ramp assembly is connected to the engine.

17. The tensioner of claim 15, wherein the spring force constants of the blade spring and the ramp assembly spring are selected such that, when the tensioner is exposed to high chain loads, the blade shoe flattens and the second end of the blade shoe slides down the ramp such that the ramp rotates and increases a resisting torque of the ramp assembly spring until the ramp assembly spring and the blade spring achieve a force balance.

18. The tensioner of claim 15 wherein the spring force constants of the blade spring and the ramp assembly spring are selected such that, when the tensioner is exposed to low chain loads, an arc radius of the blade shoe decreases and the second end of the blade shoe slides up the ramp such that the ramp rotates and decreases a resisting torque of the ramp assembly spring until the ramp assembly spring and the blade spring achieve a force balance.

19. The tensioner of claim 15, wherein the ramp assembly spring is a torsion spring.

* * * * *